United States Patent [19]

Janzen et al.

[11] Patent Number: 5,455,272
[45] Date of Patent: Oct. 3, 1995

[54] SPIN TRAP NITRONYL HINDERED PHENOLS

[75] Inventors: Edward G. Janzen, Oklahoma City, Okla.; Allan L. Wilcox, Campbell, Calif.

[73] Assignee: Oklahoma Medical Research Foundation, Oklahoma City, Okla.

[21] Appl. No.: 141,241

[22] Filed: Oct. 22, 1993

[51] Int. Cl.$^6$ .................. C07C 251/00; C07C 251/32; A61K 31/15
[52] U.S. Cl. .................. 514/579; 514/640; 514/645; 564/1; 564/265; 564/300
[58] Field of Search .................. 564/1, 265, 300; 514/579, 640, 645

[56] References Cited

U.S. PATENT DOCUMENTS

| | | | |
|---|---|---|---|
| 3,903,049 | 9/1975 | Saltman | 260/47 UA |
| 5,025,032 | 6/1991 | Carney et al. | 514/400 |
| 5,036,097 | 7/1991 | Floyd et al. | 514/400 |

FOREIGN PATENT DOCUMENTS

| | | | |
|---|---|---|---|
| 3173861 | 3/1991 | Japan | C07C 207/02 |
| 2137619 | 10/1984 | United Kingdom | C07C 135/00 |
| WO9222290 | 12/1994 | WIPO | A61K 31/135 |

OTHER PUBLICATIONS

Druelinger, et al.,"Photochemistry of methylenenitrones and related compounds. A study of oxaziridine and nitrene formation," *J. Heterocyclic Chem* 13:1001–1007 (1976).
Kalyanaraman, et al., "The spin trap α-phenyl N–tert–butynitrone, inhibits the oxidative modifications of low density lipoprotein," *FEBS Letters* 280:17–20 (1991).
Timmins, et al., "Free radical formation in isolated murine keratinocytes treated with organic peroxides and its modulation by antioxidants," *Carcinogenesis* 14:1615–1620 (1993).
Janzen, et al., "Locating spin traps in heterogeneous media by $^{13}$C NMR spectroscopy. Investigations in SDS micelles, DMPC vesicles, and rat liver microsomes," *J Org Chem* 54:2915–2920 (1989).
Fujii, et al., "Studies on the superoxide releasing site in plasma membranes of neutophils with ESR spin–lables," *J Biochem* 108:292–296 (1990).
Black, Shaun, "Membrane topology of the mammalian P450 cytochromes," *The FASEB J* 6:680–685 (1992).
Katsaras, et al., "Location of two antioxidants in oriented model membranes. Small–angle x–ray diffraction study," *Biophys J* 59:645–653 (1991).
Pryor, et al., "Detection of free radicals from low–temperature ozone–olefin reactions by ESR Sprin–trapping; evidence that the radical precursor is a trioxide," *J Am Chem Soc* 105:2883–2888 (1983).
Pryor, William, "Biological effects of cigarette smoke, wood smoke, and the smoke from plastics: the use of electron spin resonance," *Free Radical Biology & Medicine* 13:659–676 (1992).
Zahalka, et al., "Antioxidant activity of 1–thio–α–tocopherol and related compounds. EPR, ENDOR, and UV–visible absorption spectra of some of the derived phenoxyl radicals," *J Org Chem* 53:3739–3745 (1988).
Forrester, et al., *Organic Chemistry of Stable Free Radicals*, Academic Press, New York, N.Y., p. 294 (1968).
Doba, et al., "α–Tocopherol decay: lack of effect of oxygen," *J Chem Soc, Chemical Communication* 7:461–462 (1984).
Maguire, et al., "Electron transport between cytochrome $c$ and alpha tocopherol," *Biochemical and Biophysical Reasearch Communications* 188: 190–197 (1992).
Kosower, Edward, *Molecular Biochemistry*, McGraw–Hill Book Company, Inc., New York, N.Y., p. 168 (1962).
Janzen, et al., "The reversible thermal decomposition of triphenylmethylperoxy radical to tripheylmethyl radical and oxygen," *J Am Chem Soc* 89:1176–1183 (1967).

Primary Examiner—Peter O'Sullivan
Attorney, Agent, or Firm—Richards, Medlock & Andrews

[57] ABSTRACT

The invention is the use of nitronyl substituted hindered phenols as antioxidants in therapeutic applications. In the preferred embodiment the compositions have the general formula:

$$HO-\text{C}_6H_2(R_3)(R_4)-C(R_1)=N^+(R_2)-O^-$$

Wherein $R_1$ is hydrogen, an alkyl or an aryl and $R_2$ is an alkyl or an aryl; $R_3$ is an alkyl; and $R_4$ is an alkyl. Further, the invention relates to novel compositions useful as antioxidants. The novel compounds include: 2,6-di-tert-butyl-4-(N-tert-octyl)nitronyl phenol (DBONP); 2,6-dimethyl-4-(N-tert-octyl)nitronyl phenol (DMONP); N-tert-octyl-C-phenyl nitrone (OPN).

2 Claims, 3 Drawing Sheets

SPIN TRAP NITRONYL HINDERED PHENOLS

TECHNICAL FIELD OF THE INVENTION

The present invention relates to novel nitronyl substituted phenols. The present invention also relates to methods using nitronyl substituted hindered phenols as antioxidants in biological systems and therapeutic applications.

BACKGROUND OF THE INVENTION

The use of antioxidants has been proposed for therapeutic treatment and for other uses such as protecting polymers such as natural rubber and synthetic rubber from oxidation. Hindered phenols occur naturally, for example tocopherols (vitamin E), and have found use as antioxidants previously. Recently, free radicals have been postulated to have significant impact in tissue injury. Evidence suggests that the free radical mechanism has a significant impact on vascular injury and damage affecting nerve cells.

The use of phenylbutyl nitrone compositions for the treatment of oxidative tissue damage and gastric ulceration has been disclosed in U.S. Pat. Nos. 5,025,032 and 5,036,097 entitled "Phenylbutyl Nitrone Compositions and Methods For Treatment of Oxidative Tissue Damage" and "Phenylbutyl Nitrone Compositions and Methods for Prevention of Gastric Ulceration", respectively.

Research has demonstrated that nitrones select a location in membrane models and microsomes which is as polar and/or as protic as pure methanol as discussed in E. G. Janzen et al., "Locating spin traps in heterogeneous media by $^{13}$C NMR spectroscopy. Investigations in SDS micelles, DMPC vesicles and rat liver microsomes", *J. Org. Chem.* 54:2915–2920 (1989). Thus, it is suggested that antioxidant molecules must be precisely located in the same volume compartment as where the free radical event occurs, or else the free radicals will not be quenched. Heretofore, such molecules have not been available. Therefore, development of new families of antioxidant molecules is necessary in order to provide molecules which will be effective against free radical damage at different biological sites. There has also been a need to provide antioxidant compositions which have no known toxic effect while providing a more effective free radical spin trap.

The present invention offers the advantages of a spin trap agent with no known toxic effects. Further, the invention offers the advantage of providing compounds highly efficient in the quenching of free radicals.

SUMMARY OF THE INVENTION

The present invention relates to the use of particular antioxidants in therapeutic treatment. These compositions have the following general formula:

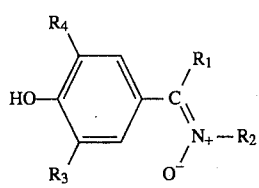

wherein R1 is a hydrogen, an aryl, or an alkyl and R2 is an alkyl or an aryl group. R1 can be any alkyl group, straight chain or branched, with or without double or triple bonds, with or without polar functions (e.g., esters, alcohols, halides, carboxylic acid, aldehydes, carboxamides, aralkyl, amino or nucleic acids). R2 can contain single, double or triple bonds and may also include polar constituents (e.g., esters, alcohols, halides, carboxylic acids, aldehydes, carboxamides, aralkyl, amino or nucleic acids). R2 can also be an aryl including substituted aryls, heterocyclic, polycyclic or acyclic. R3 and R4 can be hydrogen or any alkyl group, either straight chain or branched, preferably 1 to 4 carbons. R3 and R4 are preferably alkyls from 1 to 4 carbons in length. R3 and R4 are usually the same group. Based on animal studies the dosage of these compounds is in the range of 25 to 250 mg/kg. In the preferred embodiment, the range is between 25 and 125 mg/kg depending upon the dosage required to capture the free radical. One or more of the above compounds useful in the present invention can be mixed together in the same dose.

The present invention also relates to the use of compounds of a general formula:

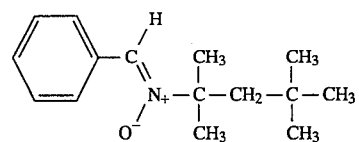

Based upon animal studies, the dosage in the range of 25 to 250 mg/kg is useful. In the preferred embodiment, the range is between 25 to 125 mg/kg.

The present invention also relates to the use of compounds of the general formula:

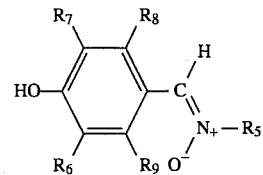

wherein R5, R6, R7, R8 and R9 are alkyl groups, and preferably R5, R6, R7, R8 and R9 are alkyls of 1 to 4 carbons. It is believed that these compounds would be useful in a dosage range of from about 25 mg to about 250 mg/kg of body weight.

Another aspect of the present invention relates to novel compounds of the formulas useful as spin traps in biological systems:

(a) N-tert-octyl C-phenyl nitrone ("OPN")

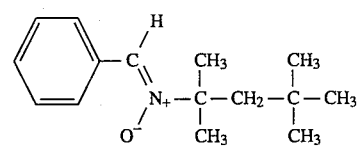

(b) 2,6-di-tert-butyl-4-(N-tert-octyl) nitronyl phenol ("DBONP")

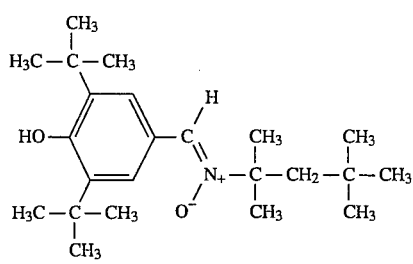

(c) 2,6-dimethyl-4-(N-tert-octyl) nitronyl phenol ("DMONP")

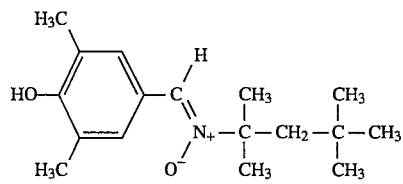

and (d) compounds of the general formula

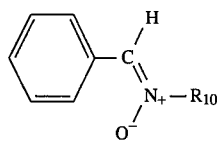

wherein $R_{10}$ is an alkyl 8 or more carbons in length. Such compounds are to be used in the method of the present invention in a dosage from 25 to 250 mg/kg, preferably from about 25 to 125 mg/kg, and more preferably from about 25 to about 50 mg/kg.

BRIEF DESCRIPTION OF THE DRAWINGS

The invention will be more fully appreciated from the following description taken in conjunction with the accompanying drawings, in which.

DETAILED DESCRIPTION OF THE INVENTION

Figure 1:
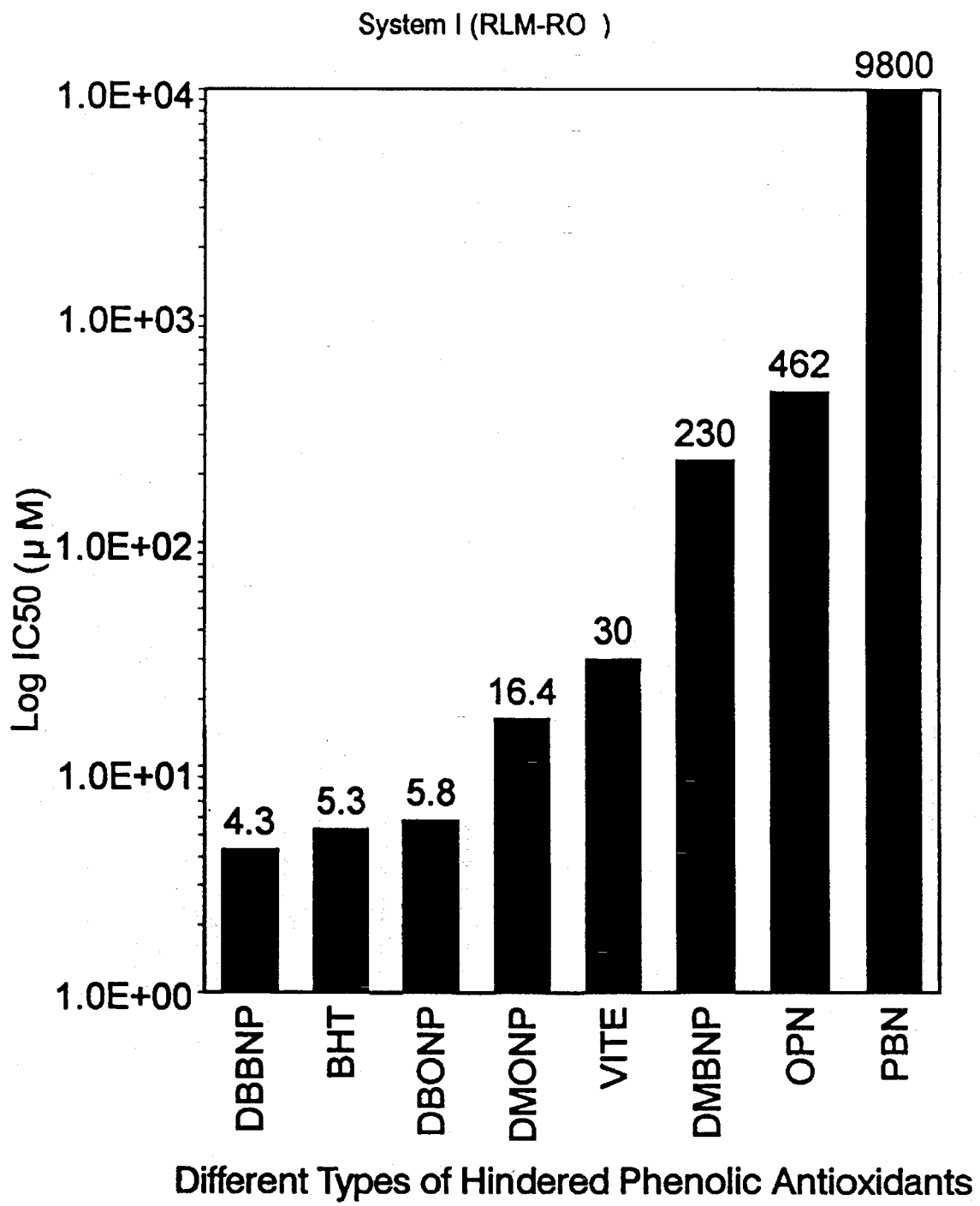
FIG. 1 is a graphical representation of inhibitor concentration for 50% inhibition ($IC_{50}$) using rat liver microsomes wherein LPO (liquid peroxidation) was initiated by tert butoxyl radicals and MDA (malondialdehyde) production was monitored by treatment with thiobarbituric acid.

As used herein a free radical scavenger or spin trap reagent (compound) is a molecule which will form a stable complex with a free radical. A carbon centered free radical is a molecule in which the free radical is localized on a carbon atom. As result of this chemical bond formation with a spin trap, the free radical is no longer damaging to cells.

Antioxidant activity has been long studied in lubricating oils by the automobile industry. The general principles and mechanisms from the lubricating oil studies has been accepted for lipid peroxidation in tissue membranes. In addition, without being bound to any particular theory we believe that there are some specific considerations which are specific to biological systems. Reactive radicals which can be damaging to tissue constituents are easily quenched by the phenolic hydrogen which is easily removed by most free radicals.

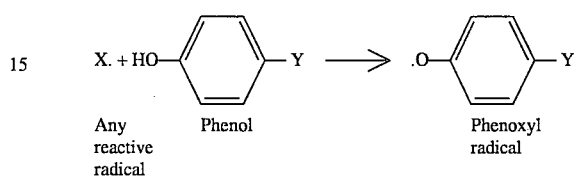

Any reactive radical    Phenol    Phenoxyl radical

This reaction produces non-damaging radicals, that is radicals that are resonance stabilized and have little reactivity. The phenoxyl radicals, in general, have been observed to disappear without creating obvious biological damage.

It has been found in biological systems that phenoxyl radicals which are stabilized by steric hinderance due to groups at the 2-and 6-position have an added advantage that they persist long enough to trap other radicals thereby quenching two radicals. For example, it has been found that 2,6-di-tert-butyl phenols produce 2,6-di-tert-butyl phenoxyl radicals which are stabilized due to the steric hinderance of the tert-butyl groups. The hindered phenoxyl has the advantage that they persist long enough to trap other radicals.

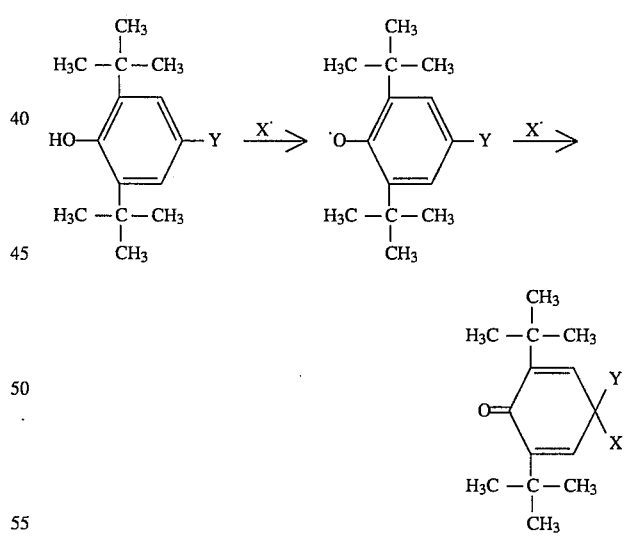

To increase the efficiency of the antioxidant activity and achieve maximum potential, it is desirable to utilize a compound which produces a high concentration of the hindered phenoxyl which will be available to capture the additional free radicals.

It is preferred that the compounds used in the present application have a reasonably long lifetime to increase efficiency. The rate of the first reaction depends upon the concentration of phenol and free radical. The rate of the first reaction is the first reaction rate constant times the concentration of the phenol times the concentration of free radicals. The rate of the second reaction depends on the concentration of the hindered phenoxyl and concentration of free radical. The reaction rate of the second reaction is the value of the second reaction rate constant, times the concentration of phenoxyl times the concentration of free radical. Thus, it is beneficial to use compounds which result in maximum concentration of phenoxyl.

The appropriate choice of the substituent in the 4-position (Y) can increase the lifetime of the hindered phenoxyl radical produced. The groups in the 4-position which stabilize the hindered phenoxyl radicals also reduce the reaction rate of the radical with oxygen thereby preventing formation of potentially damaging peroxyl radicals. For example:

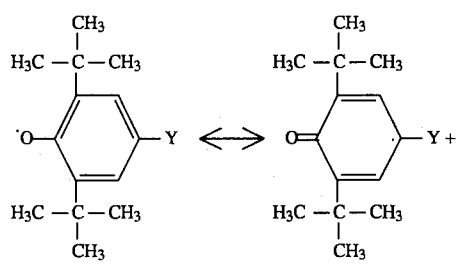

The reaction with oxygen at the 4-position can be hindered by several methods. For example, steric hinderance may be utilized, and generally, the reaction is slowed but not entirely eliminated.

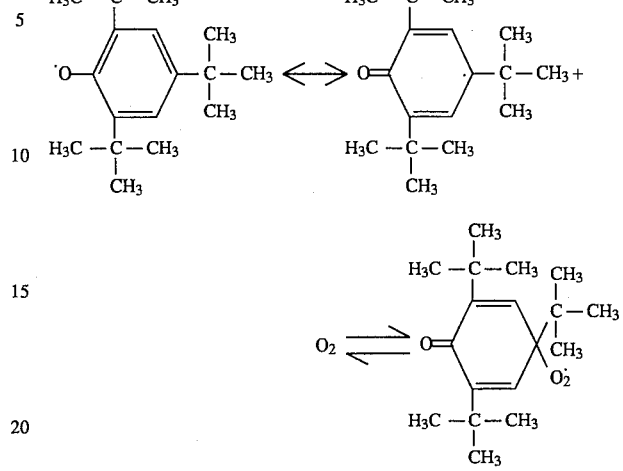

Another method is to provide resonance with the carbon in the 4-position. When the ethylenic bond is obtained, a completely stable phenoxyl radical is obtained. Thus, groups capable of strong resonance with the phenoxyl function stabilize the phenoxyl radical and prevent an addition reaction with oxygen.

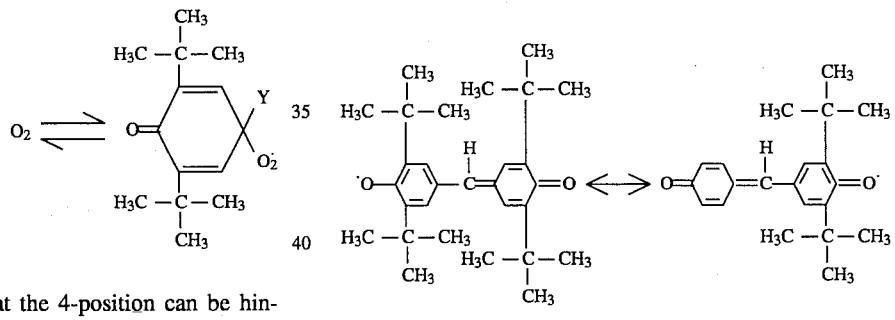

Another method of stabilization is the addition of a strained ring or rings within the phenoxyl radical adduct. Thus, when Y is a phenoxyl ring such as α-tocophenoxyl addition of oxygen is not favored. It is believed that the strained bicyclic ring structure in the peroxyl radical is a high energy product, and the formation of the peroxyl from oxygen is very unfavorable.

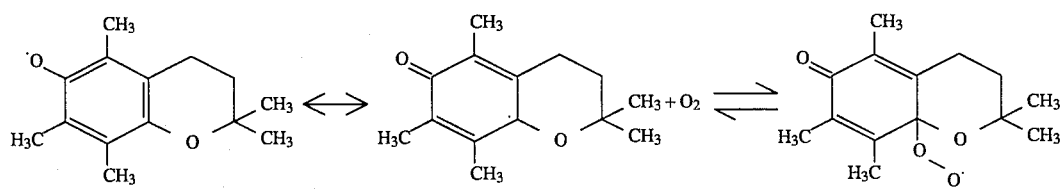

These phenoxyl radicals with strained rings can be beneficial because although they will not readily react with oxygen radicals, reactions may proceed with other peroxyl radicals to form stable adducts.

Compounds which are useful in the present invention have the following general formula:

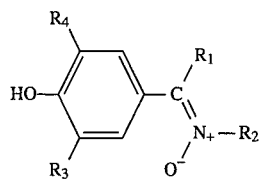

where R1 is hydrogen, an aryl, or an alkyl and R2 is an alkyl or an aryl. The alkyls of R1 and R2 can contain single, double or triple bonds and can also include polar constituents like esters, alcohol, halides, carboxylic acids, aldehydes, carboxamides, aralkyl amino or nucleic acids and others. R1 and R2 can also be an aryl including substituted aryls, heterocyclic, polycyclic or acyclic. R3 and R4 can be any alkyl group, either straight chained or branched. Preferably, R3 and R4 are alkyls from 1 to 4 carbons in length. In the preferred embodiment, R3 and R4 are the same group because synthesis of such compounds is typically easier than when R3 and R4 are different.

Other compounds useful in the present invention and which are novel compounds have the general formula:

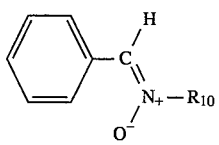

wherein in $R_{10}$ is an alkyl of 8 or more carbons.

Preferably, 2,6-di-tert-butyl-4-(N-tert-butyl) nitronyl phenol (DBBNP):

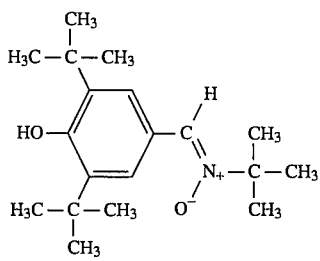

or 2,6-di-tert-butyl-4-(N-tert-octyl) nitronyl phenol (DBONP):

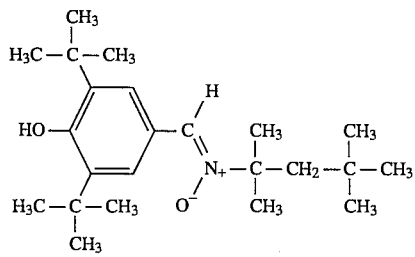

are employed in a method for quenching biological free radicals. Less preferred compounds for said method include 2,6-dimethyl-4-(N-tert-octyl) nitronyl phenol (DMONP):

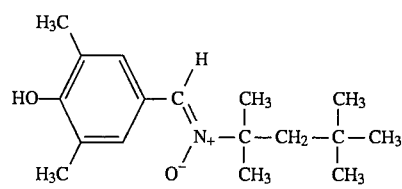

and 2,6-dimethyl-4-(N-tert-butyl) nitronyl phenol (DMBNP):

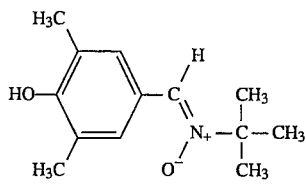

Another novel compound useful in the present invention is N-tert-octyl C-phenyl nitrone (OPN) which is represented below.

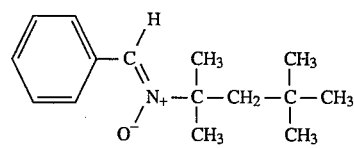

Spin traps have been implicated as useful in a number of diseases including septic shock, effect of ischemia/reperfusion, liver edema, and fatigue stress. The spin trapping efficiency is believed to be associated with not only the molecular configuration but also the relative size of the molecule in respect to the particular disease sought to be prevented or treated. Thus, certain spin trap compounds may be more effective with certain diseases than other spin trap compounds.

Spin trap compounds of the present invention were placed in pharmaceutical vehicles suitable for administration to a patient, preferably in a fat soluble substance for oral administration. The spin trap compounds of the present invention are useful in preventing or reversing edema. The compositions can also contain other active agents, such as buffering agents such as antacids or inert carriers such as lactose.

The examples demonstrate the utility of the compounds of the present invention in preventing or treating a variety of inflammation effects. Exemplary doses range from 25 to 250 mg of compound/kg of body weight in animals. The more preferred range of dosage is from about 25 to about 125 mg/kg. The effective range of dosage in humans and other mammals is expected to be between about 25 to about 50 mg/kg, and preferably between about 25 to about 35 mg/kg of body weight. The particular dosage may vary depending on the particular compound selected and the disease to be treated. Those compounds which are more effective will require a smaller dosage than those compounds which have been found to be less effective. For preferred embodiments of the invention, the effective range of dosage in humans and other mammals is expected to be in the range of: (a) from about 25 to about 50 mg/kg for DBBNP; (b) from about 25 to about 50 mg/kg body weight for DBONP; (c) from about 25 to about 50 mg/kg of body weight for DMONP; (d) from about 25 to about 50 mg/kg of body weight for DMBNP; and (e) from about 25 to about 50 mg/kg of body weight for OPN. The most preferred ranges are expected to be (a) from about 25 to about 35 mg/kg for DBBNP; (b) from about 25 to about 35 mg/kg body weight for DBONP; (c) from about 25 to about 35 mg/kg of body weight for DMONP; (d) from about 25 to about 35 mg/kg of body weight for DMBNP; and (e) from about 25 to about 35 mg/kg of body weight for OPN.

Other compounds believed to be useful include compounds of the general formula:

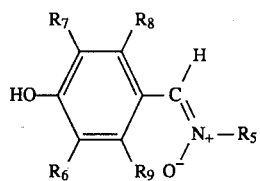

wherein R5, R6, R7, R8 and R9 are alkyl groups, and preferably alkyl groups of 1 to 4 carbon atoms. These compounds are expected to be useful in dosages from 25 to 250 mg/kg of body weight, preferably 25 to 125 mg/kg and more preferably from about 25 to about 50 mg/kg of body weight.

The compounds of the present invention are preferably administered systemically, most preferably orally, since this is the most rapid and efficient means for delivering the active compound to the site of free radical generation. The compounds can be administered at once, or can be divided into a number of smaller doses to be administered at varying intervals of times. The compounds may also be administered by other methods including intravenous, subcutaneous, topical, and intraperitoneal administration.

A preferred method of administration of the compounds of the present invention is oral delivery. The compounds may be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid, Crimogel®, or corn starch; a lubricant such as magnesium stearate or Sterotes; a glidant such as colloidal silicon dioxide; and sweetening and flavoring agents. When a capsule form is used the liquid carrier such as a fatty oil may be used. Capsules and tablets can be coated with sugar, shellac and other enteric agents as is known.

The present invention will be further understood by reference to the following nonlimiting examples demonstrating methods for determining the effectiveness of the compounds of the present invention for the treatment or prevention of inflammation effects, septic shock, effects of ischemia/reperfusion, liver edema, fatigue stress.

Compounds useful in the method present of the present invention were compared against (a) butylated hydroxy toulene ("BHT")

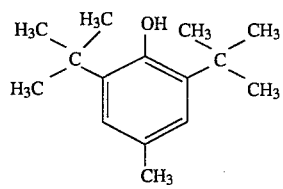

(b) α-phenyl t-butyl nitrone ("PBN")

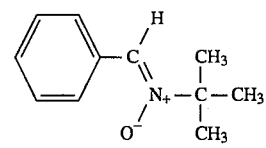

and (c) α-tocopherol (Vitamin E).

Inhibition of lipid peroxidation of rat liver microsomes has been found to be remarkably effective utilizing 4-nitronyl hindered phenols. The efficiency of these compounds was compared to the inhibition characteristics of a hindered phenol antioxidant, butylated hydroxy toluene (BHT) and α-phenyl t-butyl nitrone (PBN). Comparisons were also made with compounds useful in the present invention as well as the novel compounds of the present invention 2,6-di-tert-butyl-4-(N-tert-octyl) nitronyl phenol (DBONP); 2,6-dimethyl-4-(N-tert-octyl) nitronyl phenol (DMONP); and N-tert-octyl-C-phenyl nitrone (OPN).

EPR samples from the in vivo experiments were run on a Bruker 300E Electron Paramagnetic Resonance Spectrophotometer. Two milliliters of sample were placed in a quartz tube of 2 mm inside diameter. EPR parameters were as follows with the exception of the receiver gain and scale. These are adjusted for each sample to get the best signal.

| Receiver | | Signal Channel | |
|---|---|---|---|
| Receiver Gain | 1.00 e + 05 | Conversion | 327.68 ms |
| Phase | 0 deg | Time Const | 1310.72 ms |
| Harmonic | 1 | Sweep Time | 335.544 ms |
| Mod Frequency | 100.0000 kHz | Scale | 18 |
| Field | | Microwave | |
| Center Field | 3480.01 G | Frequency | 9.77 GHz |
| Sweep Width | 100.00 G | Power | 1.99 e + 01 mW |
| Resolution | 1024 points | | |

Example 1

Lipid peroxidation (LPO) initiated by tert-butoxy radicals

Male Sprague-Dawley rats (175–200 g) that had been maintained on commercial rat chow were starved for 24 hours, sacrificed and the livers removed. Microsomes were prepared by homogenizing the minced livers in 0.15 M potassium phosphate buffer pH 7.4 5 ml/g) and then centrifuging at 12,000×g for 15 minutes. The supernatant fraction was then centrifuged at 105,000×g for 90 minutes. The microsomal pellets were washed twice by resuspending in buffer and centrifuging at 105,000×g for 60 minutes. The microsomal pellets were kept frozen at −80° C. until ready for use. Rat liver microsome pellets were made up into microsomal suspension (MS) by adding one milliliter of 50 mM potassium phosphate buffer (pH 7.4) per gram of liver.

The protein concentration of microsomal suspensions were determined by the method of O. H. Lowry et al., *J. Biol. Chem.* 193:265–75 (1951).

Reaction samples were 1 ml (milliliter) in volume and consisted of MS (0.1 ml), 50 mM potassium phosphate buffer ($KH_2PO_4$ and $K_2HPO_4$) (pH 7.4), inhibitor in alcohol (isopropyl) and initiator (DBPO) in isopropyl alcohol. The order of addition of reagents was buffer, MS, inhibitor and finally initiator. For those experiments where the NADPH generating system is used as initiator, the reaction components were: buffer (as above), 1 mM EDTA, MS, $CCl_4$ (100 mM) and generating system. The generating system consisted of 0.5 Kornberg units of glucose-6-phosphate dehydrogenase, 5 µM glucose-6-phosphate and 0.3 mM NADPH. After all reagents were added, the test tubes were vortexed and placed in a 37° C. shaking water bath. Samples were incubated for one hour. A. Ottolenghi, *Arch. Biochem. Biophs.* 79:355 (1959). The lipid peroxidation (LPO) reaction was stopped by the addition of 0.5 ml 35% TCA (trichloroacetic acid) (weight/volume in distilled $H_2O$) and 1.0 ml 0.5% TBA (thiobarbituric acid) (w/v in distilled $H_2O$). Samples were capped with glass marbles and placed in a boiling (100° C.) water bath for 15 minutes, then cooled rapidly in an ice bath. One milliliter of distilled $H_2O$ and 2 ml chloroform were added, samples vortexed and then centrifuged at 1500 rpm for 10 minutes. The aqueous layer was read at 532 nm on a Perkin-Elmer Lambda UV/VIS spectrophotometer using a distilled $H_2O$ blank. MDA (malondialdehyde) calculations were made by the following equation:

$$(O.D. \text{ at } 532 \text{ nm} \times 22.4) \div \left( \frac{\text{mg protein/ml } MS}{0.1 \text{ ml } MS} \right) = \frac{\text{nmoles } MDA \text{ produced}}{\text{mg microsomal protein}}$$

Inhibition studies were performed by doing a concentration course of the inhibitor added to the LPO system. A stock solution of the inhibitor was made up so that various dilutions would give several (usually five) final concentrations. The original concentrated stock was usually 1M (molar) and dilutions were made to give the following final concentrations: 10, 1, 0.1, and 0.01 mM. Control samples had no inhibitor. Five samples were done for each concentration. After MDA values were calculated, percent of inhibition was determined by: average of MDA values for a given concentration divided by average of MDA values for control multiplied by 100. These results then determined if further dilutions were necessary to achieve a 50% inhibition of LPO.

| Inhibitor Concentration of 50% Inhibition ($IC_{50}$) (average of 5 experiments) | |
| --- | --- |
| BHT | 5.3 µM (interpolated between 5 and 6 µM) |
| PBN | 9800 µM (interpolated between 5 and 10 mM) |
| DBBNP | 4.3 µM (interpolated between 2.5 and 5 µM) |

| -continued | |
| --- | --- |
| Inhibitor Concentration of 50% Inhibition ($IC_{50}$) (average of 5 experiments) | |
| DBONP | 5.8 µM (interpolated between 5 and 7.5 µM) |
| DMONP | 16.4 µM (interpolated between 15 and 20 µM) |
| DMBNP | 230 µM (estimated from 250 µM experiment) |
| OPN | 462 µM (estimated from 250 and 500 µM) |
| Tocopherol (vitamin E) | 30 µM (measured) |

In this example and the following examples, $IC_{50}$ was attempted to be reached by trial and error. In the event it was missed, the $IC_{50}$ value was determined by interpolation of the results. Interpolations were made using the closest result higher than $IC_{50}$ and the closest result lower than $IC_{50}$. The reference to "measured" means that $IC_{50}$ was hit right on and thus no interpolation was required.

The test results demonstrate that the flanking tert-butyl groups in the ortho positions (2, 6) of the phenol give improved efficiency. The relative efficiency of the various compounds from the above data normalized to 1.0 for PBN can be represented as follows:

| DBBNP> | BHT> | DBONP> | DMONP> | Vit E> | DMBNP> | OPN> | PBN |
| --- | --- | --- | --- | --- | --- | --- | --- |
| 2466 | 2000 | 1828 | 646 | 354 | 46 | 24 | 1.0 |

Thus, DBBNP is about 2000 times more effective as an inhibitor of LPO in rat liver microsomes than PBN and about 20% better than BHT. Even taking into account experimental precision, one can conclude that DBBNP is at least as good as BHT and probably better.

Example 2

LPO initiated by NADPH catalyzed cytochrome-P450 metabolism of $CCl_4$

An amount equal to 0.09 mmole spin trap was weighed into a test-tube to give a final concentration of 30 mM. To this container was added 14 µl $^{13}CCL_4$ (to produce a final concentration of 50 mM). After shaking to dissolve the spin trap, 2.35 ml of 50 mM potassium phosphate buffer at pH 7.4 ($KH_2PO_4$ and $K_2HPO_4$) was added plus 0.3 ml microsomal suspension. The solution was vortexed and preincubated for 10 minutes at room temperature (25° C.). At this point, 0.3 ml NADPH generating system (0.5 Kornberg units of glucose-6-phosphate dehydrogenase, 5 µM glucose-6-phosphate and 0.3 mM NADPH) was added to start the reaction. After incubation for 15 min at room temperature, 1.0 ml toluene was added and the system vortexed. Following centrifugation for 30 minutes at 3000 rpm (Sorvell GLC-4 with swinging bucket rotor H1000) approximately 500 µl supernatant solution is removed and transferred to an EPR quartz tube. The solution was degassed for 10 minutes with argon and scanned by EPR spectrometry.

The following results were obtained:

| Inhibitor Concentration of 50% Inhibition ($IC_{50}$) (average of 5 experiments) | |
| --- | --- |
| BHT | 55 µM (interpolated between 50 and 100 µM) |
| PBN | 17,500 µM (interpolated between 10 and 25 mM) |
| DBBNP | 53 µM (interpolated between 50 and 100 µM) |

-continued

Inhibitor Concentration of 50% Inhibition (IC$_{50}$)
(average of 5 experiments)

| | |
|---|---|
| DBONP | 35 μM (interpolated between 20 and 40 μM) |
| DMBNP | 710 μM (interpolated between 500 and 750 μM) |
| DMONP | 60 μM (interpolated between 40 and 80 μM) |
| OPN | 6500 μM (interpolated between 4 and 8 mM) |

Example 3

Rat Brain Microsomes

Similar tests were performed with rat brain microsomes using the TBA test for MDA production as the result of LPO. Results on the same compounds were as follows:

| Inhibitor Concentration for 50% Inhibition (IC$_{50}$) | |
|---|---|
| BHT | (not available) |
| PBN | 1000 μM |
| DBBNP | 0.7 μM |
| DBONP | 0.3 μM |
| DMONP | 70 μM |
| DMBNP | 600 μM |
| OPN | 76 μM |

Although BHT was not available for this test it is not believed that it would be particularly effective with this particular system.

The data obtained demonstrates that DBBNP and DBONP are very good inhibitors in these systems.

| | IC$_{50}$ | | |
|---|---|---|---|
| | RLM (I) | RLM (II) | RBM (III) |
| DBBNP | 4.3 μM | 53 μM | 0.7 μM (700 nM) |
| DBONP | 5.8 μM | 35 μM | 0.3 μM (300 nM) |

Figure 2:
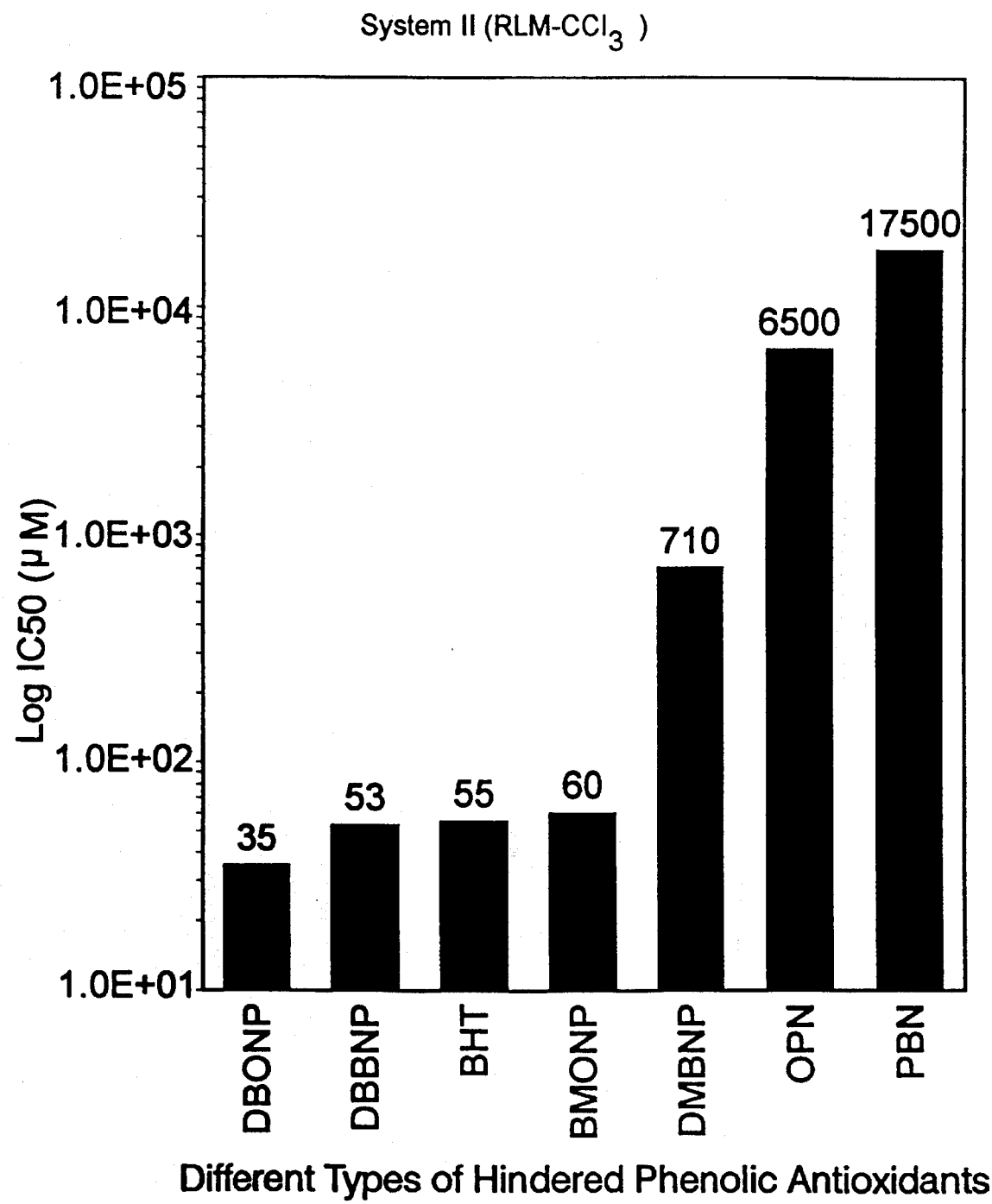
FIG. 2 is a graphical representation of inhibitor concentration for 50% inhibition ($IC_{50}$) using rat liver microsomes where LPO is initiated by NADPH catalyzed cytochrome-P450 metabolism of $CCl_4$ based on the TBA (thiobarbituric acid) test for MDA production.
Figure 3:
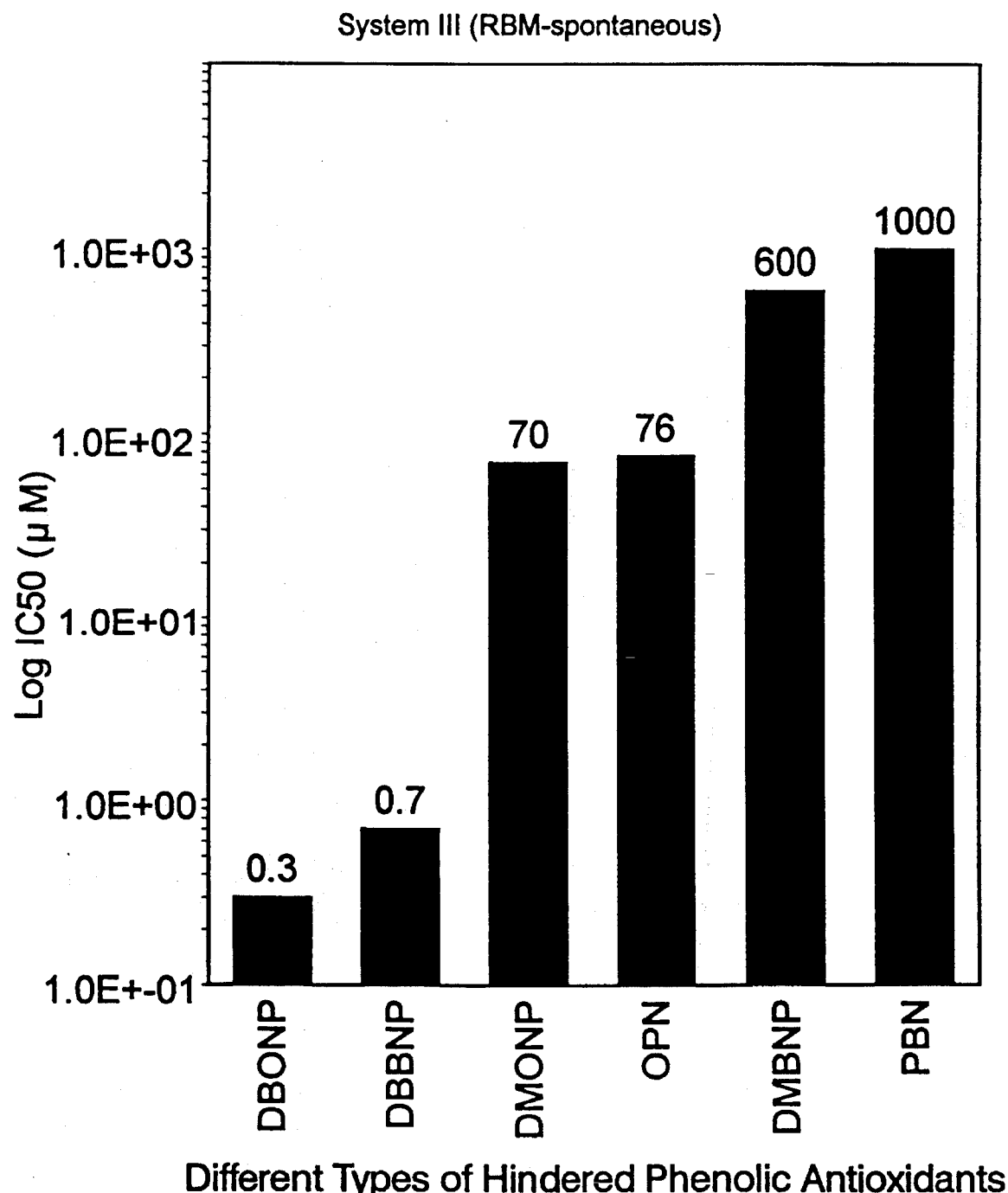
FIG. 3 is a graphical representation of inhibitor concentration for 50% inhibition ($IC_{50}$) of LPO for rat brain microsomes using the TBA test for MDA production.

The above data in Examples 1, 2 and 3 are graphically represented, respectively, in FIGS. 1, 2 and 3. It should be noted that in these graphs the smaller result is better.

FIG. 1 is a graphical representation of inhibitor concentration for 50% inhibition (IC$_{50}$) using rat liver microsomes wherein LPO (liquid peroxidation) was initiated by tert-butoxyl radicals and MDA (malondialdehyde) production was monitored by treatment with thiobarbituric acid (TBA). The relative effectiveness between the compounds can be seen, with the smaller bars indicating better performance.

FIG. 2 is a graphical representation of inhibitor concentration for 50% inhibition (IC$_{50}$) using rat liver microsomes where LPO is initiated by NADPH catalyzed cytochrome-P450 metabolism of $CCl_4$ based on the TBA (thiobarbituric acid) test for MDA production.

FIG. 3 is a graphical representation of inhibitor concentration for 50% inhibition (IC$_{50}$) of LPO for rat brain microsomes using the TBA test for MDA production.

SYNTHESIS OF NOVEL COMPOUNDS

Synthesis of the novel compounds of the present invention were carried out following the general procedures below.

2-Methyl-2-nitropropane was prepared as follows: potassium permanganate (650 g, 4.1 mole) was dissolved in 3 L $H_2O$ and t-butyl amine (100 g, 1.4 mole) added over 30 minutes. The temperature was brought to 90° C. and the reaction allowed to cool for 4 hours with stirring by mechanical stirrer. A still head and condenser was attached to a side arm of the 5 L three neck round bottom flask and the product distilled off. Diethyl ether was added and the product washed 2× with 5% HCl, 1× with $H_2O$, 1× with saturated NaCl. The organic layer was dried over $MgSO_4$ and the solvent stripped leaving 112.6 g (1.09 mole, 78%) clear liquid.

4-Nitro-2,2,4-trimethylpentane was prepared as follows: potassium permanganate (380 g, 2.4 mole) was added in portions to t-octyl amine (50 g, 0.4 mole) and $MgSO_4 \times 7H_2O$ (60 g) in 250 mL $H_2O$ with mechanical stirring. The temperature was maintained below 30° C. with an ice bath. Stirring and cooling was continued for 2.5 hours after which the reaction was allowed to warm to room temperature and stirred for 48 hours. The reaction was filtered and the residue washed with pentane. The organic layer was separated, dried over $MgSO_4$ and pentane distilled at atmospheric pressure. The product was distilled at <1 mm to give 30 g (47%) of clear liquid.

t-Octyl hydroxylamine was prepared as follows: 4-nitro-2,2,4-trimethylpentane (10.35 g, 0.065 mole) with $NH_4Cl$ (3.49 g, 0.065 mole) was cooled in 75% $THF/H_2O$ with stirring by a magnetic stir bar to 10° C. and zinc (25.5 g, 0.39 mole) added in portions to maintain the temperature at 10°–15° C. (one hour). Reaction was allowed to warm to room temperature and stirred for one hour. The mixture was filtered and the solvent stripped leaving 9.25 g (98%) clear liquid. The hydroxylamine was used immediately in subsequent reactions.

Example 4

Procedure for the synthesis of 2,6-dimethyl-4-(N tert-octyl) nitronyl phenol (DMONP) is similar to other 4-nitronylphenols. t-Octyl hydroxylamine (4.35 g, 0.03 mole) and 3,5-dimethyl-4-hydroxybenzaldehyde (2.25 g, 0.015 mole) were refluxed in 60 mL benzene with 5 mg pTsOH for 15 hours. TLC on silica gel (20% EtOAc/hexane) showed 1:1 aldehyde (rf=0.47) to nitrone (rf=0.29). t-Octyl hydroxylamine (4.35 g, 0.03 mole) was added and the reaction stirred for 18 hours. TLC showed no aldehyde, mostly nitrone, and a few less polar impurities. The solvent was stripped, the residue applied to a silica gel column, and product eluted with mixtures of hexane/EtOAc to give 3.74 g (90%) crystals with a melting point of 113°–114° C.

Example 5

2,6-di-tert-butyl-4-(N-tert-octyl) nitronyl phenol (DBONP) can be prepared as follows. t-Octyl hydroylamine and 3,5-di-tert-butyl-4-hydroxybenzaldehyde are refluxed in benzene with p-TsOH for sufficient time to begin the reaction. t-Octyl hydroylamine can then be added and the reaction stirred until complete reaction has occurred. The solvent is then stripped, the residue applied to a silica gel column, and product eluted with mixtures of hexane/EtOAc which should produce DBONP crystals with a melting point of 153°–154° C.

Example 6

N-tert-octyl C-phenyl nitrone (OPN) can be prepared as follows: t-octyl hydroxylamine and 4-hydroxybenzaldehyde should be refluxed in benzene with p-TsOH for sufficient time to begin the reaction. Additional t-octyl hydroxylamine can be added and the reactants stirred until completion of the reaction. The solvent can then be stripped, the residue applied to silica gel column and product eluted with mixture of hexane/EtOAc which should give OPN crystals.

While the invention has been described by several specific examples, it will be understood that the invention is not limited to the specific examples herein.

We claim:

1. A compound according to the formula:

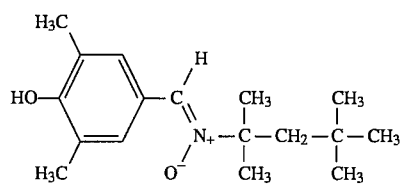

2. A pharmaceutical composition comprising a pharmacologically effective amount of a compound as claimed in claim 1, and a pharmaceutically acceptable carrier.

* * * * *